United States Patent
Kittelmann (10) Patent No.: US 12,403,039 B2
(45) Date of Patent: Sep. 2, 2025

(54) LASER SOURCE FOR AN OPHTHALMIC SURGICAL SYSTEM

(71) Applicant: Alcon Inc., Fribourg (CH)

(72) Inventor: Olaf Kittelmann, Berlin (DE)

(73) Assignee: ALCON INC., Fribourg (CH)

( * ) Notice: Subject to any disclaimer, the term of this patent is extended or adjusted under 35 U.S.C. 154(b) by 481 days.

(21) Appl. No.: 17/823,304

(22) Filed: Aug. 30, 2022

(65) Prior Publication Data

US 2023/0066391 A1 Mar. 2, 2023

Related U.S. Application Data (60) Provisional application No. 63/240,102, filed on Sep. 2, 2021.

(51) Int. Cl.
| | |
|---|---|
| *H01S 3/23* | (2006.01) |
| *A61F 9/008* | (2006.01) |
| *B23K 26/0622* | (2014.01) |
| *H01S 3/00* | (2006.01) |

(52) U.S. Cl.
CPC ........ *A61F 9/0084* (2013.01); *B23K 26/0624* (2015.10); *H01S 3/0057* (2013.01); *H01S 3/235* (2013.01); *A61F 2009/00872* (2013.01)

(58) Field of Classification Search
CPC ...... H01S 3/235; H01S 3/2325; H01S 3/0057; A61F 9/0084; A61F 2009/00872; B23K 26/0624
See application file for complete search history.

(56) References Cited

U.S. PATENT DOCUMENTS

| | | | |
|---|---|---|---|
| 9,664,849 B2 * | 5/2017 | Dong | H01S 3/06729 |
| 10,020,632 B2 * | 7/2018 | Courjaud | H01S 3/2308 |
| 10,067,289 B2 * | 9/2018 | Dong | H01S 3/06708 |
| 11,495,934 B1 * | 11/2022 | Richardson | H01S 3/005 |
| 2008/0112041 A1 | 5/2008 | Clubley et al. | |

(Continued)

FOREIGN PATENT DOCUMENTS

EP 2468224 A1 6/2012

OTHER PUBLICATIONS

Hanieh Fattahi, et al., High-power, 1-ps, all-Yb:YAG thin-disk regenerative amplifer, Optics Letters, Mar. 15, 2016, 1126-1129, 41-6.

(Continued)

*Primary Examiner* — Shirley X Jian (57) ABSTRACT

A laser source for an ophthalmic surgical system includes a femtosecond seeder, an amplifier, a femtosecond pulse portion, a nanosecond pulse portion, and one or more switches. The femtosecond seeder generates femtosecond pulses. The amplifier amplifies laser pulses, which include the femtosecond pulses and nanosecond pulses. The amplifier amplifies the laser pulses by amplifying the femtosecond pulses and generating and amplifying the nanosecond pulses. The femtosecond pulse portion alters and outputs the femtosecond pulses, and the nanosecond pulse portion alters and outputs the nanosecond pulses. The switches receive the laser pulses from the amplifier, and direct the laser pulses to the femtosecond pulse portion or the nanosecond pulse portion. In other embodiments, the laser source includes a femtosecond seeder and a nanosecond seeder that generates the nanosecond pulses.

22 Claims, 3 Drawing Sheets

(56) References Cited

U.S. PATENT DOCUMENTS

| | | | |
|---|---|---|---|
| 2009/0242531 A1* | 10/2009 | Baird | B23K 26/0622 |
| | | | 219/121.81 |
| 2010/0241107 A1 | 9/2010 | Vogler et al. | |
| 2010/0298818 A1 | 11/2010 | Lenzner et al. | |
| 2011/0249318 A1 | 10/2011 | Mccahon et al. | |
| 2016/0291247 A1* | 10/2016 | Dong | G02B 6/02009 |
| 2017/0343730 A1* | 11/2017 | Dong | G02B 6/03633 |

OTHER PUBLICATIONS

Lasersoft Brochure, Katana Technologies, Downloaded Aug. 19, 2021, Germany, www.katanalaser.com.

Marandi Atabak, et al., Femotosecond + Nanosecond Multiple Pulse train from a Thin Disk Regenerative Amplifier, Conference on Lasers and Electro-Optics, Jan. 1, 2019, p. 1, paragraph 1-p. 2, paragraph 1; figures 1,2, 140, Washington, D.C.

Marandi, et al., Femtosecond + Nanosecond Multiple Pulse Train from a Thin Disk Regenerative Amplifier, Conference on Lasers and Electro-Optics, Jan. 1, 2019, p. 1, paragraph 1-p. 2, paragraph 1; figures 1, 2, 140.

Pulzar Z1 Brochure, CUSTOMVIS, 2011, Australia, www.customvis.com.

* cited by examiner

LASER SOURCE FOR AN OPHTHALMIC SURGICAL SYSTEM

TECHNICAL FIELD

The present disclosure relates generally to ophthalmic surgical systems, and more particularly to a laser source for an ophthalmic surgical system.

BACKGROUND

Laser-assisted in situ keratomileusis (LASIK) is a type of refractive surgery that reshapes the cornea to correct refractive errors such as myopia, hyperopia, and astigmatism. During surgery, a femtosecond laser photodisrupts corneal tissue to create a flap. The flap is folded back, revealing the stroma. Then, an excimer laser (such as a 193-nanometer laser) ablates the tissue with nanosecond pulses to reshape the corneal stroma to correct the refractive error.

BRIEF SUMMARY

In certain embodiments, a laser source for an ophthalmic surgical system includes a femtosecond seeder, an amplifier, a femtosecond pulse portion, a nanosecond pulse portion, and one or more switches. The femtosecond seeder generates femtosecond pulses. The amplifier amplifies laser pulses, which include the femtosecond pulses and nanosecond pulses. The amplifier amplifies the laser pulses by amplifying the femtosecond pulses and generating and amplifying the nanosecond pulses. The femtosecond pulse portion alters and outputs the femtosecond pulses, and the nanosecond pulse portion alters and outputs the nanosecond pulses. The switches receive the laser pulses from the amplifier, and direct the laser pulses to the femtosecond pulse portion or the nanosecond pulse portion.

Embodiments may include none, one, some, or all of the following features: The laser source further comprises control electronics that: determine if a request is for the femtosecond pulses or the nanosecond pulses; and instruct the switches to direct the laser pulses to the femtosecond pulse portion or the nanosecond pulse portion in accordance with the request. The amplifier further generates the nanosecond pulses by Q-switching. The amplifier includes: an optical switch that operates as a Q-switch; and a pump laser synchronized with the optical switch. The amplifier is a regenerative amplifier, a fiber amplifier, or a multi-pass amplifier chain. The nanosecond pulse portion includes a frequency converter that converts near infrared wavelengths to ultraviolet wavelengths to yield ultraviolet nanosecond pulses. The nanosecond pulse portion includes a nanosecond ablation head that outputs the nanosecond pulses. The femtosecond pulse portion alters and outputs the femtosecond pulses by outputting near infrared femtosecond pulses. The femtosecond pulse portion alters and outputs the femtosecond pulses by outputting ultraviolet femtosecond pulses. The femtosecond pulse portion alters and outputs the femtosecond pulses by outputting near infrared femtosecond pulses and ultraviolet femtosecond pulses. The femtosecond pulse portion may include: a near infrared femtosecond optic head that outputs the near infrared femtosecond pulses; and an ultraviolet femtosecond optic head that outputs the ultraviolet femtosecond pulses. The femtosecond pulse portion includes: a frequency converter that converts near infrared wavelengths to ultraviolet wavelengths to yield ultraviolet femtosecond pulses; and an ultraviolet femtosecond optic head that outputs the ultraviolet femtosecond pulses.

In certain embodiments, a laser source for an ophthalmic surgical system includes femtosecond and nanosecond seeders, an amplifier, a femtosecond pulse portion, a nanosecond pulse portion, and one or more switches. The seeders generate laser pulses comprising femtosecond pulses and nanosecond pulses. The femtosecond seeder generates the femtosecond pulses, and the nanosecond seeder generates the nanosecond pulses. The amplifier amplifies the femtosecond pulses and the nanosecond pulses. The femtosecond pulse portion alters and outputs the femtosecond pulses, and the nanosecond pulse portion alters and outputs the nanosecond pulses. The switches receive the laser pulses from the amplifier, and direct the laser pulses to the femtosecond pulse portion or the nanosecond pulse portion.

Embodiments may include none, one, some, or all of the following features: The laser source further comprises control electronics that: determine if a request is for the femtosecond pulses or the nanosecond pulses; and instruct the switches to direct the laser pulses to the femtosecond pulse portion or the nanosecond pulse portion in accordance with the request. The amplifier is a regenerative amplifier, a fiber amplifier, or a multi-pass amplifier chain. The nanosecond pulse portion includes a frequency converter that converts near infrared wavelengths to ultraviolet wavelengths to yield ultraviolet nanosecond pulses. The nanosecond pulse portion includes a nanosecond ablation head that outputs the nanosecond pulses. The femtosecond pulse portion alters and outputs the femtosecond pulses by outputting near infrared femtosecond pulses and ultraviolet femtosecond pulses. The femtosecond pulse portion may include: a near infrared femtosecond optic head that outputs the near infrared femtosecond pulses; and an ultraviolet femtosecond optic head that outputs the ultraviolet femtosecond pulses. The femtosecond pulse portion includes: a frequency converter that converts near infrared wavelengths to ultraviolet wavelengths to yield ultraviolet femtosecond pulses; and an ultraviolet femtosecond optic head that outputs the ultraviolet femtosecond pulses.

In certain embodiments, a laser source for an ophthalmic surgical system includes a femtosecond seeder, an amplifier, a femtosecond pulse portion, a nanosecond pulse portion, one or more switches, and control electronics. The femtosecond seeder generates femtosecond pulses. The amplifier amplifies laser pulses, which include the femtosecond pulses and nanosecond pulses. The amplifier amplifies the laser pulses by amplifying the femtosecond pulses and generating and amplifying the nanosecond pulses. The amplifier is a regenerative amplifier, a fiber amplifier, or a multi-pass amplifier chain that generates the nanosecond pulses by Q-switching. The amplifier includes: an optical switch that operates as a Q-switch; and a pump laser synchronized with the optical switch. The femtosecond pulse portion alters and outputs the femtosecond pulses as near infrared femtosecond pulses and ultraviolet femtosecond pulses. The femtosecond pulse portion includes: a near infrared femtosecond optic head that outputs the near infrared femtosecond pulses; a frequency converter that converts near infrared wavelengths to ultraviolet wavelengths to yield ultraviolet femtosecond pulses; and an ultraviolet femtosecond optic head that outputs the ultraviolet femtosecond pulses. The nanosecond pulse portion alters and outputs the nanosecond pulses. The nanosecond pulse portion includes a frequency converter that converts near infrared wavelengths to ultraviolet wavelengths to yield ultraviolet nanosecond pulses, and a nanosecond ablation head that outputs the nanosecond pulses. The switches receive the laser pulses from the amplifier, and direct the laser pulses to the femtosecond pulse portion or the nanosecond pulse portion. The control electronics determine if a request is for the femtosecond pulses or the nanosecond pulses, and instruct the switches to direct the laser pulses to the femtosecond pulse portion or the nanosecond pulse portion in accordance with the request.

In certain embodiments, a laser source for an ophthalmic surgical system includes femtosecond and nanosecond seeders, an amplifier, a femtosecond pulse portion, a nanosecond pulse portion, one or more switches, and control electronics. The seeders generate laser pulses comprising femtosecond pulses and nanosecond pulses. The femtosecond seeder generates the femtosecond pulses, and the nanosecond seeder generates the nanosecond pulses. The amplifier is a regenerative amplifier, a fiber amplifier, or a multi-pass amplifier chain that amplifies the femtosecond pulses and the nanosecond pulses. The femtosecond pulse portion alters and outputs the femtosecond pulses as near infrared femtosecond pulses and ultraviolet femtosecond pulses. The femtosecond pulse portion includes: a near infrared femtosecond optic head that outputs the near infrared femtosecond pulses; a frequency converter that converts near infrared wavelengths to ultraviolet wavelengths to yield ultraviolet femtosecond pulses; and an ultraviolet femtosecond optic head that outputs the ultraviolet femtosecond pulses. The nanosecond pulse portion alters and outputs the nanosecond pulses. The nanosecond pulse portion includes a frequency converter that converts near infrared wavelengths to ultraviolet wavelengths to yield ultraviolet nanosecond pulses, and a nanosecond ablation head that outputs the nanosecond pulses. The switches receive the laser pulses from the amplifier, and direct the laser pulses to the femtosecond pulse portion or the nanosecond pulse portion. The control electronics determine if a request is for the femtosecond pulses or the nanosecond pulses, and instruct the switches to direct the laser pulses to the femtosecond pulse portion or the nanosecond pulse portion in accordance with the request.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Known LASIK systems use femtosecond and excimer lasers to perform the surgery. However, using both types of lasers requires more room and costs more. Moreover, excimer lasers have disadvantages, e.g., they require high voltage, utilize a toxic gas (ArF gas), need complex beam shapers, create ozone, and are bulky. In addition, excimer lasers use radiation with a wavelength that is affected by humidity and oxygen in the air, which affects the ablation rate and requires a humidity-controlled environment and nitrogen purging of the beam paths.

In certain embodiments, a solid-state laser source provides femtosecond laser pulses for performing flap creation and other intrastromal procedures and nanosecond laser pulses for performing ablation procedures. The laser source uses the same components for generating femtosecond and nanosecond pulses, thus avoiding the problems of using two lasers. Moreover, the laser source is not an excimer laser, thus avoiding the disadvantages of excimer lasers.

Figure 1:
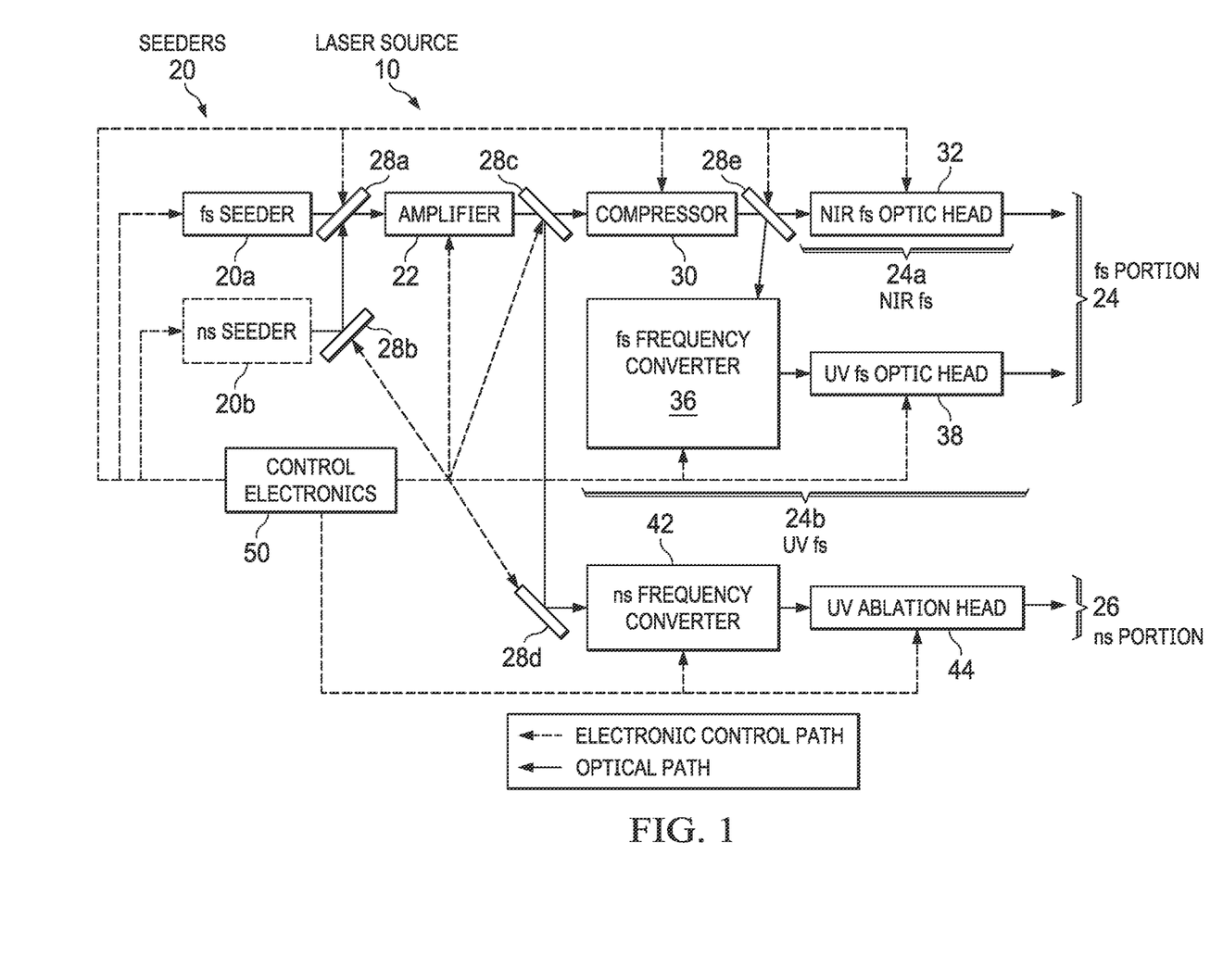
FIG. 1 illustrates an example of a laser source that provides femtosecond and nanosecond laser pulses for an ophthalmic surgical system, according to certain embodiments.

FIG. 1 illustrates an example of a laser source 10 that provides femtosecond and nanosecond laser pulses for an ophthalmic surgical system, according to certain embodiments. In the illustrated example, laser source 10 is a solid-state laser source that includes seeders 20 (which include femtosecond seeder 20a and/or nanosecond seeder 20b), amplifier 22, femtosecond portion 24, nanosecond portion 26, switches 28 (e.g., mirrors 28a-e), and control electronics 50, coupled (e.g., optically, electrically, and/or mechanically) as shown. Femtosecond portion 24 includes a compressor 30, a near infrared (NIR) femtosecond portion 24a, and an ultraviolet (UV) femtosecond portion 24b, coupled as shown. NIR femtosecond portion 24a includes a NIR femtosecond optic head 32. UV femtosecond portion 24b includes a femtosecond frequency converter 36 and a UV femtosecond optic head 38, coupled as shown. Nanosecond portion 26 includes a nanosecond frequency converter 42 and a UV ablation head 44, coupled as shown.

As an example of an overview of operation, seeder(s) 20 (e.g., femtosecond seeder 20a and optionally nanosecond seeder 20b) generate laser pulses, and amplifier 22 amplifies the laser pulses. Switches 28 receive the laser pulses from amplifier 22 and direct the laser pulses to femtosecond pulse portion 24 or nanosecond pulse portion 26. In certain embodiments, control electronics 50 may determine if a request is for femtosecond or nanosecond pulses, and instruct switches 28 to direct the laser pulses to the femtosecond 24 or nanosecond 26 pulse portion in accordance with the request. Femtosecond pulse portion 24 outputs femtosecond pulses, or nanosecond pulse portion 26 outputs nanosecond pulses.

Turning to the details of the example, laser source 10 includes seeders 20, e.g., femtosecond seeder 20a and/or nanosecond seeder 20b. In certain embodiments, laser source 10 includes femtosecond and nanosecond seeders 20 that generate femtosecond and nanosecond pulses. In other embodiments, laser source 10 includes a femtosecond seeder 20a, but not a nanosecond seeder 20b, so only femtosecond pulses are generated in a seeder. Amplifier 22 (which may be a regenerative amplifier) can generate the nanosecond pulses by, e.g., Q-switching.

Amplifier 22 may comprise one or more cascaded amplifiers, and may comprise a regenerative amplifier, a fiber amplifier, or a multi-pass amplifier chain. If laser source 10 includes femtosecond and nanosecond seeders 20, a fiber amplifier may be used. If laser source 10 does not include a nanosecond seeder 20b, a regenerative amplifier can generate the nanosecond pulses by Q-switching. The regenerative amplifier may have the gain medium (e.g., a solid-state medium) in an optical resonator where pulses make multiple round-trip passes. An optical switch controls the number of passes, allowing for a large number of passes that yield high amplification. An example of amplifier 22 is described in more detail with reference to FIG. 2.

In the example, the pulses from seeder(s) 20 have near infrared (NIR) wavelengths, e.g., 1000 to 1700 nanometers (nm). Wavelength/frequency converters transform the NIR wavelengths to UV wavelengths, e.g., 340 to 360 nm for femtosecond pulses and 200 to 220 nm, such as 204 to 216 nm (deep UV or DUV), for nanosecond pulses. Frequency converters may include cascaded stages of optical non-linear crystals and may be designed to match fundamental and required target wavelengths by, e.g., generating the Third Harmonic of the fundamental femtosecond pulses or generating Fifth Harmonic of the fundamental nanosecond pulses.

Nanosecond portion 26 includes nanosecond frequency converter 42 and UV nanosecond ablation head 44. Frequency converter 42 transforms the nanosecond pulses from NIR wavelengths (e.g., 1020 to 1080 nm) to deep UV wavelengths (e.g., 204 to 216 nm). UV nanosecond ablation head 44 outputs nanosecond pulses, which may be used to ablate tissue such as corneal tissue.

Femtosecond portion 24 provides NIR and UV femtosecond pulses, which may be used to treat tissue, such as corneal tissue, by photodisruption. In the example, compressor 30 compresses laser pulses from amplifier 22 to femtosecond pulse durations. NIR femtosecond portion 24a includes a NIR femtosecond optic head 32 that outputs NIR femtosecond pulses. UV femtosecond portion 24b includes femtosecond frequency converter 36 and UV femtosecond optic head 38. Frequency converter 36 transforms the femtosecond pulses from NIR wavelengths (e.g., 1020 to 1080 nm) to UV wavelengths (e.g., 340 to 360 nm) via, e.g., frequency tripling. UV femtosecond optic head 38 outputs UV femtosecond pulses.

Switches 28 such as mirrors 28a-e direct laser pulses to components in response to instructions from control electronics 50. A switch 28 may be any suitable optical elements that can switch laser pulses, e.g., a mirror, Pockels cell and Polarizer, acousto-optic modulator, micro-electro-mechanical system, or galvo mirror.

Control electronics 50 sends instructions to control the components of laser source 10. In certain embodiments, control electronics 50 may determine if a request is for femtosecond or nanosecond pulses, and instruct switches 28 to direct the laser pulses to the femtosecond 24 or nanosecond 26 pulse portion in accordance with the request.

Figure 2:
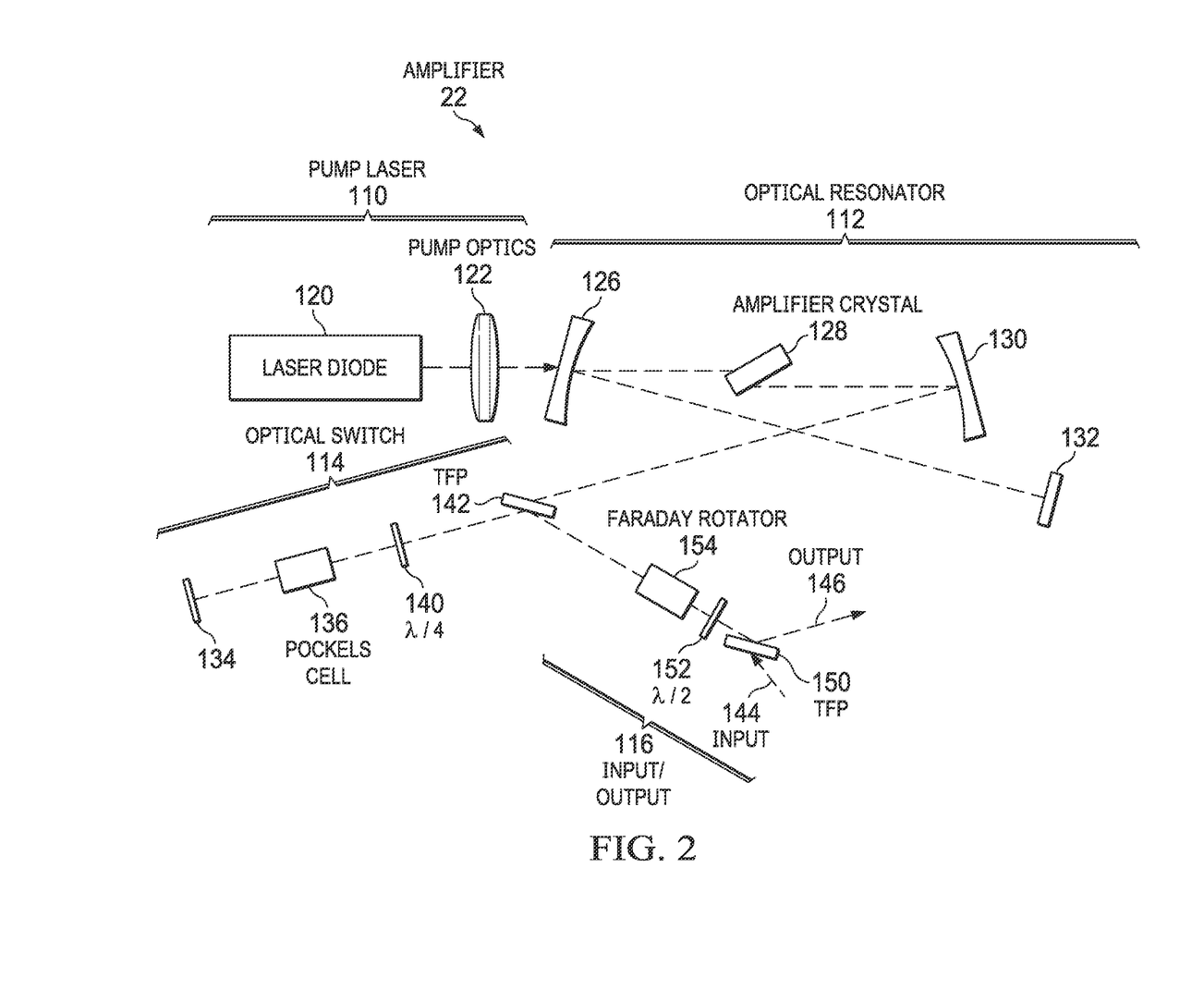
FIG. 2 illustrates an example of an amplifier that may be used in the laser source of FIG. 1.

FIG. 2 illustrates an example of an amplifier 22 that may be used in laser source 10 of FIG. 1. In the example, amplifier 22 is a regenerative amplifier that includes a pump laser 110, an optical resonator 112, and an input/output (I/O) 116, coupled (e.g., optically) as shown. Seed laser 110 includes a laser diode 120 and pump optics 122, coupled as shown. Optical resonator 112 includes an optical switch 114, mirrors 126, 130, 132, 134 and an amplifier crystal 128, coupled as shown. Optical switch 114 includes a mirror 134, an electro-optic device such as a Pockels cell 136, a quarter-wave plate 140, and a thin-film polarizer (TFP) 142, coupled as shown. In another embodiment, an acousto-optic modulator may be used as the optical switch. Input/output 116 includes an input 144, an output 146, a TFP 150, a half-wave plate 140, and a Faraday rotator 154, coupled as shown.

As an overview of operation, input 144 provides seed pulses to optical resonator 112 via input/output (I/O) 116. Optical resonator 112 amplifies laser pulses when the pulses make round trips through amplifier crystal 128 within the resonator. Optical switch 114 controls the entrance and exit of a pulse into and out of optical resonator 112, which controls the amplification of the pulse. Input/output 116 directs pulses to exit amplifier 22 via output 146.

Turning to details of the example, pump laser 110 provides energy to activate (pump) amplifier crystal 128 to increase the energy of the circulating pulses by several orders of magnitude. A greater number of round trips results in more amplification. Mirrors 126, 130, 132, 134 of optical resonator 112 direct pulses through amplifier crystal 128 and to optical switch 114. A mirror may be any suitable optical element that reflects or otherwise directs laser pulses. Amplifier crystal 128 amplifies laser pulses and may be any suitable laser crystal, e.g., Ytterbium or Neodymium doped materials.

Optical switch 114 may be an electro-optic or acousto-optic switch. Pockels cell 136, quarter-wave plate 140, and thin-film polarizer (TFP) 142 operate as an optical switch to transmit or reflect pulses, in order to switch pulses between optical resonator 112 and input/output 116. This controls the amount of amplification. Input 144 of input/output 116 feeds pulses into amplifier 22, and output 146 allows pulses out of amplifier 22. Faraday rotator 154 and half-wave plate 152 operate as an optical diode to separate the input and output pulses.

In certain embodiments, such as where there is no nanosecond seeder, amplifier 22 (which may be a regenerative amplifier) can generate the nanosecond pulses by, e.g., Q-switching. Amplifier 22 operates as a Q-switched laser resonator, where optical switch 114 acts as Q-switch. Q-switching modulates the intracavity losses and the Q factor of the laser resonator. Q-switching can be supported by pump laser 110 synchronized with optical switch 114. Pump laser 110 may operate as a pulsed pump source or a continuous wave pump laser.

Figure 3:
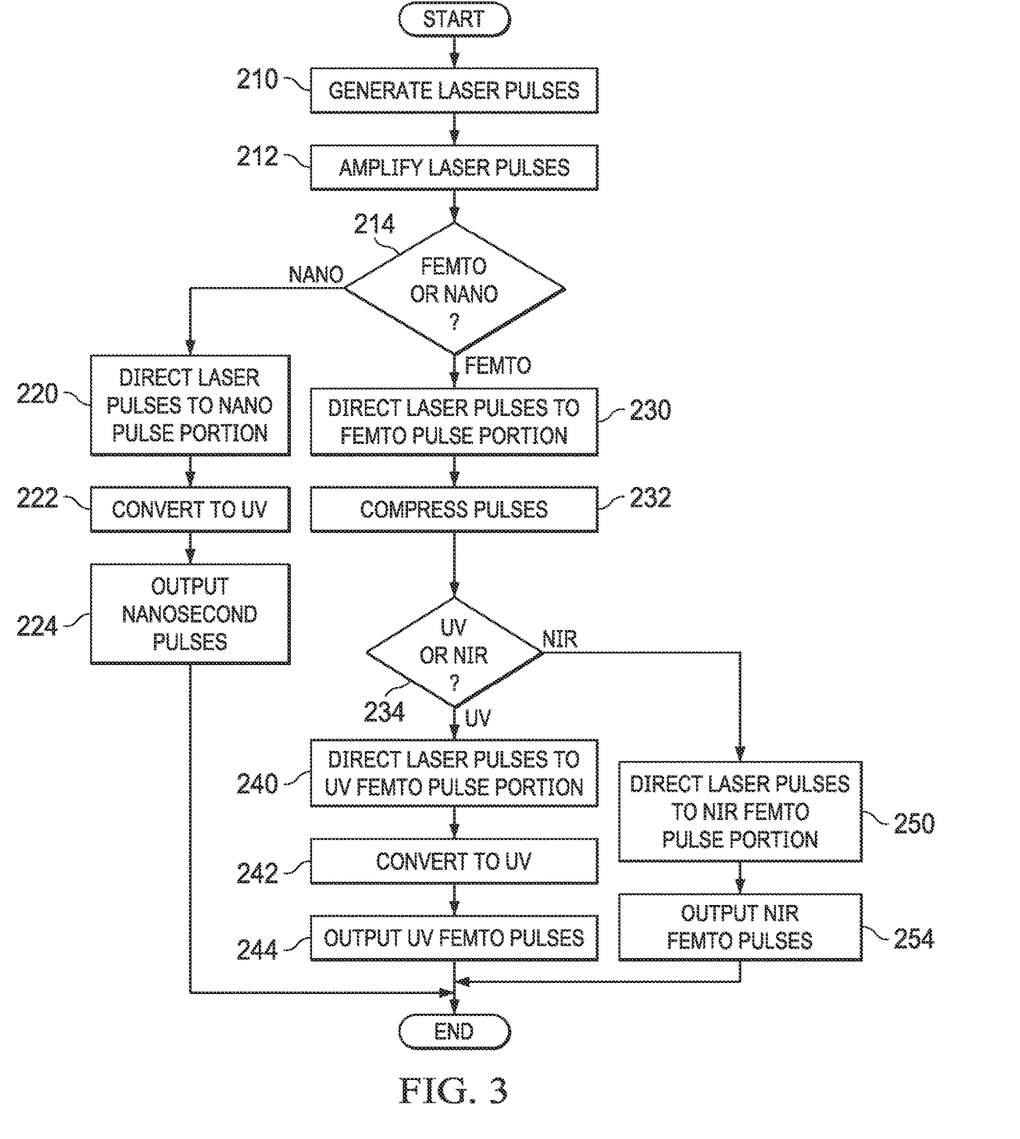
FIG. 3 illustrates an example of a method for providing laser pulses for a laser ophthalmic surgical system that may be performed by the laser source of FIG. 1, according to certain embodiments.

FIG. 3 illustrates an example of a method for providing laser pulses for a laser ophthalmic surgical system that may be performed by the laser source of FIG. 1, according to certain embodiments. The method starts at step 210, where one or more seeders generate laser pulses. In certain embodiments, the laser source includes femtosecond and nanosecond seeders that generate femtosecond and nanosecond pulses. In other embodiments, the laser source includes a femtosecond seeder, but not a nanosecond seeder, so only femtosecond pulses are generated, and an amplifier generates the nanosecond pulses.

An amplifier amplifies the laser pulses at step 212. If the laser source includes only a femtosecond seeder, but not a nanosecond seeder, the amplifier also generates the nanosecond pulses via Q-switching. The laser source may be requested to provide femtosecond or nanosecond pulses at step 214. In certain embodiments, control electronics determine if the request is for femtosecond or nanosecond pulses, and instruct switches to direct the laser pulses to a femtosecond or nanosecond pulse portion in accordance with the request.

If nanosecond pulses are requested at step 214, the method proceeds to step 220, where the laser pulses are directed to the nanosecond pulse portion. A frequency converter converts near infrared (NIR) wavelengths to ultraviolet (UV) wavelengths to yield UV nanosecond pulses at step 222. A nanosecond ablation head outputs the nanosecond pulses at step 224. The pulses may be used to ablate tissue. The method then ends.

If femtosecond pulses are requested at step 214, the method proceeds to step 230, where the laser pulses are directed to the femtosecond pulse portion. A compressor compresses the NIR femtosecond pulses at step 234 to a femtosecond pulse duration. The laser source may be requested to provide UV or NIR femtosecond pulses at step 232. In certain embodiments, control electronics determine if the request is for UV or NIR femtosecond pulses, and instruct switches to direct the laser pulses to the UV or NIR femtosecond pulse portion in accordance with the request.

If UV femtosecond pulses are requested at step 234, the method proceeds to step 240, where the laser pulses are directed to the UV femtosecond pulse portion. A frequency converter converts near infrared wavelengths to ultraviolet wavelengths to yield UV femtosecond pulses at step 242. A UV femtosecond optic head outputs the UV femtosecond pulses at step 244. The pulses may be used to photodisrupt tissue. The method then ends.

If NIR femtosecond pulses are requested at step 234, the method proceeds to step 250, where the laser pulses are directed to the NIR femtosecond pulse portion. A NIR femtosecond optic head outputs the NIR femtosecond pulses at step 254. The pulses may be used to photodisrupt tissue. The method then ends.

A component (such as control electronics 50) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A laser source for an ophthalmic surgical system, the laser source comprising:
    a femtosecond seeder configured to generate a plurality of femtosecond pulses; and
    an amplifier configured to:
        generate a plurality of nanosecond pulses; and
        amplify a plurality of laser pulses, the plurality of laser pulses comprising the plurality of femtosecond pulses and the plurality of nanosecond pulses, the amplifier configured to amplify the plurality of laser pulses by:
            amplifying the plurality of femtosecond pulses generated by the femtosecond seeder; and
            amplifying the plurality of nanosecond pulses generated by the amplifier;
    a femtosecond pulse portion configured to alter and output the plurality of femtosecond pulses;
    a nanosecond pulse portion configured to alter and output the plurality of nanosecond pulses; and
    one or more switches configured to:
        receive the plurality of laser pulses from the amplifier; and
        direct the plurality of laser pulses to the femtosecond pulse portion or the nanosecond pulse portion.

2. The laser source of claim 1, further comprising control electronics configured to:
    determine if a request is for the plurality of femtosecond pulses or the plurality of nanosecond pulses; and
    instruct the one or more switches to direct the plurality of laser pulses to the femtosecond pulse portion or the nanosecond pulse portion in accordance with the request.

3. The laser source of claim 1, the amplifier further configured to generate the plurality of nanosecond pulses by Q-switching.

4. The laser source of claim 3, the amplifier comprising:
    an optical switch configured to operate as a Q-switch; and
    a pump laser synchronized with the optical switch.

5. The laser source of claim 1, the amplifier selected from the following:
    a regenerative amplifier, a fiber amplifier, or a multi-pass amplifier chain.

6. The laser source of claim 1, the nanosecond pulse portion comprising:
    a frequency converter configured to convert near infrared wavelengths to ultraviolet wavelengths to yield a plurality of ultraviolet nanosecond pulses.

7. The laser source of claim 1, the nanosecond pulse portion comprising:
    a nanosecond ablation head configured to output the plurality of nanosecond pulses.

8. The laser source of claim 1, the femtosecond pulse portion configured to alter and output the plurality of femtosecond pulses by outputting a plurality of near infrared femtosecond pulses.

9. The laser source of claim 1, the femtosecond pulse portion configured to alter and output the plurality of femtosecond pulses by outputting a plurality of ultraviolet femtosecond pulses.

10. The laser source of claim 1, the femtosecond pulse portion configured to alter and output the plurality of femtosecond pulses by:
outputting a plurality of near infrared femtosecond pulses; and
outputting a plurality of ultraviolet femtosecond pulses.

11. The laser source of claim 10, the femtosecond pulse portion comprising:
a near infrared femtosecond optic head configured to output the plurality of near infrared femtosecond pulses; and
an ultraviolet femtosecond optic head configured to output the plurality of ultraviolet femtosecond pulses.

12. The laser source of claim 1, the femtosecond pulse portion comprising:
a frequency converter configured to convert near infrared wavelengths to ultraviolet wavelengths to yield a plurality of ultraviolet femtosecond pulses; and
an ultraviolet femtosecond optic head configured to output the plurality of ultraviolet femtosecond pulses.

13. A laser source for an ophthalmic surgical system, the laser source comprising:
a femtosecond seeder configured to generate a plurality of femtosecond pulses;
an amplifier comprising:
an optical switch configured to operate as a Q-switch; and
a pump laser synchronized with the optical switch;
the amplifier configured to:
generate a plurality of nanosecond pulses by q-switching; and
amplify a plurality of laser pulses, the plurality of laser pulses comprising the plurality of femtosecond pulses and the plurality of nanosecond pulses, the amplifier configured to amplify the plurality of laser pulses by:
amplifying the plurality of femtosecond pulses generated by the femtosecond seeder; and
amplifying the plurality of nanosecond pulses generated by the amplifier;
a femtosecond pulse portion configured to alter and output the plurality of femtosecond pulses;
a nanosecond pulse portion configured to alter and output the plurality of nanosecond pulses; and
one or more switches configured to:
receive the plurality of laser pulses from the amplifier; and
direct the plurality of laser pulses to the femtosecond pulse portion or the nanosecond pulse portion.

14. The laser source of claim 13, further comprising control electronics configured to:
determine if a request is for the plurality of femtosecond pulses or the plurality of nanosecond pulses; and
instruct the one or more switches to direct the plurality of laser pulses to the femtosecond pulse portion or the nanosecond pulse portion in accordance with the request.

15. The laser source of claim 13, the amplifier selected from the following: a regenerative amplifier, a fiber amplifier, or a multi-pass amplifier chain.

16. The laser source of claim 13, the nanosecond pulse portion comprising:
a frequency converter configured to convert near infrared wavelengths to ultraviolet wavelengths to yield a plurality of ultraviolet nanosecond pulses.

17. The laser source of claim 13, the nanosecond pulse portion comprising:
a nanosecond ablation head configured to output the plurality of nanosecond pulses.

18. The laser source of claim 13, the femtosecond pulse portion configured to output the plurality of femtosecond pulses by:
outputting a plurality of near infrared femtosecond pulses; and
outputting a plurality of ultraviolet femtosecond pulses.

19. The laser source of claim 18, the femtosecond pulse portion comprising:
a near infrared femtosecond optic head configured to output the plurality of near infrared femtosecond pulses; and
an ultraviolet femtosecond optic head configured to output the plurality of ultraviolet femtosecond pulses.

20. The laser source of claim 13, the femtosecond pulse portion comprising:
a frequency converter configured to convert near infrared wavelengths to ultraviolet wavelengths to yield a plurality of ultraviolet femtosecond pulses; and
an ultraviolet femtosecond optic head configured to output the plurality of ultraviolet femtosecond pulses.

21. A laser source for an ophthalmic surgical system, the laser source comprising:
a femtosecond seeder configured to generate a plurality of femtosecond pulses; and
an amplifier configured to amplify a plurality of laser pulses, the plurality of laser pulses comprising the plurality of femtosecond pulses and a plurality of nanosecond pulses, the amplifier comprising a regenerative amplifier comprising:
an optical switch configured to operate as a Q-switch; and
a pump laser synchronized with the optical switch, the amplifier configured to amplify the plurality of laser pulses by:
amplifying the plurality of femtosecond pulses generated by the femtosecond seeder;
generating the plurality of nanosecond pulses by Q-switching; and
amplifying the plurality of nanosecond pulses generated by the amplifier;
a femtosecond pulse portion configured to alter and output the plurality of femtosecond pulses by outputting a plurality of near infrared femtosecond pulses and a plurality of ultraviolet femtosecond pulses, the femtosecond pulse portion comprising:
a near infrared femtosecond optic head configured to output the plurality of near infrared femtosecond pulses;
a frequency converter configured to convert near infrared wavelengths to ultraviolet wavelengths to yield a plurality of ultraviolet femtosecond pulses; and
an ultraviolet femtosecond optic head configured to output the plurality of ultraviolet femtosecond pulses;
a nanosecond pulse portion configured to alter and output the plurality of nanosecond pulses, the nanosecond pulse portion comprising:
a frequency converter configured to convert near infrared wavelengths to ultraviolet wavelengths to yield a plurality of ultraviolet nanosecond pulses; and a nanosecond ablation head configured to output the plurality of nanosecond pulses;
one or more switches configured to:
receive the plurality of laser pulses from the amplifier; and
direct the plurality of laser pulses to the femtosecond pulse portion or the nanosecond pulse portion; and
control electronics configured to:
determine if a request is for the plurality of femtosecond pulses or the plurality of nanosecond pulses; and
instruct the one or more switches to direct the plurality of laser pulses to the femtosecond pulse portion or the nanosecond pulse portion in accordance with the request.

22. A laser source for an ophthalmic surgical system, the laser source comprising:
a femtosecond seeder configured to generate a plurality of femtosecond pulses;
an amplifier comprising:
an optical switch configured to operate as a Q-switch; and
a pump laser synchronized with the optical switch;
the amplifier configured to:
generate a plurality of nanosecond pulses by q-switching; and
amplify a plurality of laser pulses, the plurality of laser pulses comprising the plurality of femtosecond pulses and the plurality of nanosecond pulses, the amplifier configured to amplify the plurality of laser pulses by:
amplifying the plurality of femtosecond pulses generated by the femtosecond seeder; and
amplifying the plurality of nanosecond pulses generated by the amplifier, the amplifier comprising a regenerative amplifier, a fiber amplifier, or a multi-pass amplifier chain;
a femtosecond pulse portion configured to alter and output the plurality of femtosecond pulses by outputting a plurality of near infrared femtosecond pulses and a plurality of ultraviolet femtosecond pulses, the femtosecond pulse portion comprising:
a near infrared femtosecond optic head configured to output the plurality of near infrared femtosecond pulses;
a frequency converter configured to convert near infrared wavelengths to ultraviolet wavelengths to yield a plurality of ultraviolet femtosecond pulses; and
an ultraviolet femtosecond optic head configured to output the plurality of ultraviolet femtosecond pulses;
a nanosecond pulse portion configured to alter and output the plurality of nanosecond pulses, the nanosecond pulse portion comprising:
a frequency converter configured to convert near infrared wavelengths to ultraviolet wavelengths to yield a plurality of ultraviolet nanosecond pulses; and
a nanosecond ablation head configured to output the plurality of nanosecond pulses;
one or more switches configured to:
receive the plurality of laser pulses from the amplifier; and
direct the plurality of laser pulses to the femtosecond pulse portion or the nanosecond pulse portion; and
control electronics configured to:
determine if a request is for the plurality of femtosecond pulses or the plurality of nanosecond pulses; and
instruct the one or more switches to direct the plurality of laser pulses to the femtosecond pulse portion or the nanosecond pulse portion in accordance with the request.

* * * * *